United States Patent [19]

Casadio et al.

[11] Patent Number: 4,774,325

[45] Date of Patent: Sep. 27, 1988

[54] NEW 8-SUBSTITUTED NUCLEOSIDE AND PURINE DERIVATIVES, THE PROCESS FOR THE PREPARATION THEREOF AND THE PHARMACEUTICAL COMPOSITIONS CONTAINING THEM

[75] Inventors: Silvano Casadio, Milan; Duccio Favara, Como; Amedeo Omodei-Salé, Voghera Pavia; Ezio Pantó, Milan, all of Italy

[73] Assignee: Pierrel Spa, Naples, Italy

[21] Appl. No.: 776,472

[22] Filed: Sep. 16, 1985

[30] Foreign Application Priority Data

Sep. 20, 1984 [IT] Italy ............................. 22739 A/84

[51] Int. Cl.$^4$ ...................... C07H 19/20; A61K 31/70
[52] U.S. Cl. ........................................ 536/26; 536/27; 536/18.3; 536/120; 544/265; 544/267
[58] Field of Search ............... 536/26, 27, 18.3, 120; 544/265, 267

[56] References Cited

U.S. PATENT DOCUMENTS

| | | | |
|---|---|---|---|
| 2,819,260 | 1/1958 | Monson et al. | 536/120 |
| 3,391,196 | 7/1968 | Earing et al. | 536/18.3 |
| 3,712,885 | 1/1973 | Weimann et al. | 536/28 |
| 4,048,307 | 9/1977 | Yokota et al. | 536/28 |
| 4,446,313 | 5/1984 | Dix et al. | 536/18.3 |

FOREIGN PATENT DOCUMENTS

| | | | |
|---|---|---|---|
| 0143557 | 6/1985 | European Pat. Off. | 514/262 |
| 0111312 | 5/1900 | Fed. Rep. of Germany | 544/267 |
| 2631046 | 1/1977 | Fed. Rep. of Germany | 536/26 |
| 0883056 | 11/1981 | U.S.S.R. | 536/27 |

OTHER PUBLICATIONS

Chemical Abstracts, vol. 84, 1976, p. 587, Abstract No. 105653c, Columbus, Ohio, U.S. & JP-A-75 15 800 (Dainippon Pharmaceutical Co., Lt.), 07-06-1975.
R. M. Acheson, An Introduction to the Chemistry of Heterocyclic Compounds, Wiley-Interscience, 1967, New York, p. 338.
J. March, Adv. Organic Chemistry, Reaction + Mechanism + Structure, McGraw Hill, New York, 1968, p. 328.

*Primary Examiner*—J. R. Brown
*Assistant Examiner*—L. Eric Crane
*Attorney, Agent, or Firm*—Murray and Whisenhunt

[57] ABSTRACT

New 8-substituted nucleoside and purine derivatives of the general formula:

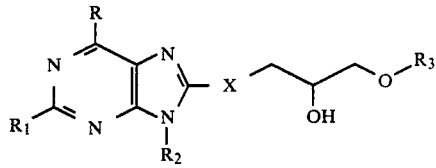

wherein R represents an amino group or an hydroxy group possibly in the corresponding keto tautomeric form, $R_1$ is hydrogen or an amino group, $R_2$ is hydrogen or a β-D-ribofuranosyl radical wherein the primary hydroxy group and/or the two secondary hydroxy groups may be derivatized, $R_3$ is an optionally substituted aryl or monocyclic heteroaryl radical and, X is —O— or —S—. The new compounds have antihyperlipaemic activity.

10 Claims, No Drawings

NEW 8-SUBSTITUTED NUCLEOSIDE AND PURINE DERIVATIVES, THE PROCESS FOR THE PREPARATION THEREOF AND THE PHARMACEUTICAL COMPOSITIONS CONTAINING THEM

This invention relates to new 8-substituted nucleoside and purine derivatives which are useful as antihyperlipaemics, the process for the preparation thereof and the pharmaceutical compositions containing them.

The new 8-substituted nucleoside and purine derivatives of the present invention may be represented by general formula I:

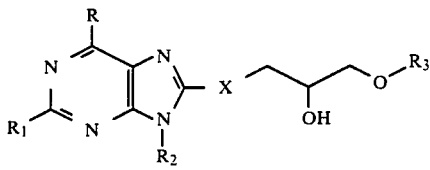

wherein R is an amino group or an hydroxy group possibly in the corresponding keto tautomeric form, $R_1$ is hydrogen or an amino group, $R_2$ is hydrogen or a beta-D-ribofuranosyl group wherein the primary hydroxy group at the 5'-position may be replaced by an acyloxy group, wherein the acyl moiety may be derived from an aliphatic, aromatic or heterocyclic carboxylic acid, a carbamyloxy group or a mono-, di- or tri-phosphate group, and the secondary hydroxy groups at the 3' and 2' positions may be replaced by an acyloxy group, wherein the acyl moiety is derived from an aliphatic carboxylic acid, or a carbamyloxy group, $R_3$ is an optionally substituted aryl or monocyclic heteroaryl group, and X is sulfur or oxygen.

In the present specification and claims the term "aliphatic carboxylic acid" identifies a straight or branched, saturated or unsaturated aliphatic carboxylic acid containing from 2 to 20 carbon atoms and, according to a preferred embodiment of the invention, a straight or branched saturated aliphatic carboxylic acid containing from 2 to 6 carbon atoms such as for instance acetic acid, propionic acid, isobutyric acid, isovaleric acid and the like.

The term "aromatic carboxylic acid" substantially refers to benzoic acid and benzoic acid derivatives wherein the phenyl ring is substituted, such as for instance 2-, 3- or 4-methyl-benzoic acid, 2-, 3- or 4-chlorobenzoic acid, 3,5-dimethylbenzoic acid, 2-, 3- or 4-methoxy-benzoic acid, 3,4,5-trimethoxybenzoic acid and the like.

The term "heterocyclic carboxylic acid" refers to heterocyclic carboxylic acids where the heterocyclic ring is a monocyclic 5- or 6-membered ring containing 1 or 2 heteroatoms independently selected from nitrogen, oxygen and sulfur, and preferably identifies the positional isomers of pyridincarboxylic acid, and more preferably 3-pyridincarboxylic acid or nicotinc acid, pyrazincarboxylic acid, 2-furancarboxylic acid and the like.

The term "optionally substituted aryl or monocyclic heteroaryl group" designates a phenyl residue or a 5- or 6-membered heteroaryl residue which contains 1 or more hetero-atoms independently selected from N, O, and S, such as for instance pyridyl, pyrazinyl, pyrimidyl, furyl, thienyl, imidazolyl, thiazolyl and 1,2,4-triazolyl, optionally bearing 1 to 3 substituents. As an example, suitable substituents may, each independently, be selected from $(C_1-C_4)$alkyl, $(C_3-C_4)$alkenyl, hydroxy, $(C_1-C_4)$alkoxy, acyloxy, $(C_3-C_4)$alkenyloxy, halogen, nitro, amino, mono- and di-$(C_1-C_4)$alkylamino, mono- or di-acylamino, carboxy, $(C_1-C_{20})$alkoxy-carbonyl, benzyloxycarbonyl, dialkylaminoethoxycarbonyl, acylaminoethoxycarbonyl, $(C_3-C_{20})$alkenyloxycarbonyl, heterocycloxycarbonyl, heterocyclylalkoxycarbonyl, carbamyl, mono- and di-$(C_1-C_4)$alkylcarbamyl, cyano, trifluoromethyl etc., where the substituents and the moieties "alkyl", "alkenyl", "alkoxy" and "alkenyloxy" in the other substituents containing said moieties may, in turn, be substituted.

A preferred group of compounds of the present invention comprises those compounds of formula I wherein R is amino and $R_1$ is hydrogen, or R is hydroxy and $R_1$ is amino or hydrogen, $R_2$ is hydrogen or beta-D-ribofuranosyl where the hydroxy groups may be derivatized as seen before, and $R_3$ and X are as defined above.

A most preferred group of compounds of the present invention comprises those compounds of formula I where R is amino, $R_1$ is hydrogen, $R_2$ is hydrogen or a beta-D-ribofuranosyl radical where the hydroxy groups may be derivatized as seen before, $R_3$ is an optionally substituted aryl residue and X is a sulfur atom.

In the above formula I the carbon atom on the side chain bearing the hydroxyl substituent may have either the R or S configuration. It has therefore to be understood that the present invention comprises both the single pure isomers and their mixtures in any proportion.

The compounds of the present invention are endowed with remarkable antihyperlipaemic activity.

Purine derivative variously substituted at the 2-, 6-, 8- and 9-positions are known in the patent as well as published literature with different pharmacological activities, such as for instance as antivirals (see for instance Belgian Patent 833,006 and EP-A-9154 and EP-A-No. 85424), as broncho-dilators (see for instance U.S. Pat. No. 3,862,189), as antitumor agents (see for instance U.S. Pat. No. 3,238,207 and Dutch patent application 67/09151) or as hypotensives (see for instance Dutch patent application 64/10101).

Furthermore there is a series of purine derivatives claiming an hypocholesteremic activity which are variously substituted at the 2-, 6- and 8-positions but are characterized by the presence of a group $-CH_2-CH(OH)-CH(OH)-COOR$ at the 9-position (see for instance the following Japanese Kokais: no. 46/39352) Farmdoc 73726 S), no. 47/19272 (Farmdoc 37338 T), no. 47/24039 (Farmdoc 44182 T), no. 48/01678 (Farmdoc 5084 U), no. 48/01679 (Farmdoc 5085 U), no. 48/16519 (Farmdoc 30279 U), no. 50/22039 (Farmdoc 56483 W) and Belgian Patent 737,949) or a group

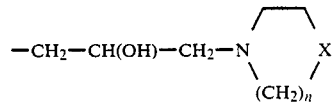

(see EP-A-52964).

The compounds of the present invention may be prepared by conventional methods easily available to any skilled chemist.

A general method for the preparation of the new 8-substituted purine or nucleoside derivatives however consists in the introduction of the side-chain at the 8-position by reacting the corresponding 8-bromo-purine or nucleoside derivative with a compound of the formula R₃O—CH₂—CH(OR')—CH₂—XH wherein $R_3$ and X are as defined before and R' is a protecting group of the hydroxy function easily removable at the end of the reaction.

When X represents an oxygen atom, the free hydroxy groups, and preferably also the amino groups on the starting purine or nucleoside substrate, must be protected to avoid competitive side reactions or deactivation of the substrate.

Protecting groups of the hydroxy functions which resulted in being particularly useful in the synthesis of the new compounds of the invention are for instance cyclic ethers and in particular tetrahydropyranyl, trityl and dimethoxytrityl.

Said protecting groups are generally introduced by conventional techniques using a polar aprotic solvent such as for instance 1,2-dimethoxyethane, tetrahydrofuran, ethyl ether, ethyl acetate and the like in the presence of an acidic catalyst such as for instance p-toluensulfonic acid.

When, on the contrary, simultaneous protection of both hydroxy groups at C-2' and C-3' is desired, the purine or nucleoside substrate is preferably reacted with acetone and anhydrous p-toluene-sulfonic acid thus converting the ribose vicinal diol in the corresponding acetonide.

Reagents which may suitably be employed in the process of the present invention for the protection of the amino groups are silyl derivatives and in particular trimethylsilyl or dimethyl t-butylsilyl halides and dimethylformamide dimethylacetal.

This latter reactant is preferred because the protection reaction of the purine base with dimethylformamide dimethylacetal in dimethylformamide gives almost quantitive yields and can be easily performed.

It has to be understood that the use of other protecting groups of both the hydroxy and the amino functions, which even if not specifically indicated or discussed here, may suitably be employed in the process of the present invention, do fall within the scope thereof.

The condensation reaction between the possible protected 8-bromopurine or nucleoside derivative and the compound of the formula R₃OCH₂CH(OR')CH₂—XH is preferably carried out in a dipolar aprotic solvent such as dimethylformamide, ethers, tetrahydrofuran, dimethylsulfoxide, etc., in the presence of a strong base such as sodium hydride, butyllithium, phenyllithium or potassium t-butoxide.

When X is a sulfur atom, the reaction may as well be carried out in protic solvents such as alcohols or water, with milder bases such as sodium or potassium hydroxides, alcoholates or carbonates.

The reaction course is monitored by conventional chromatographic method (HPLC, TLC,) and at the end of the reaction the obtained product is recovered and the protecting groups, if any, are removed. A suitable method which allows simultaneous deprotection of both the hydroxy and the amino groups is the acid hydrolysis with diluted sulfuric acid at room temperature in aqueous or alcoholic solvents.

As for the purification of the obtained product which may be carried out either before or after deprotection, suitable methods consist in conventional crystallization and chromatographic techniques (column chromatography and preparative HPLC). When X is a sulfur atom, a particularly conventional alternative method consists in reacting an 8-mercaptopurine or nucleoside derivative, easily obtainable, as an example, by reacting the corresponding 8-bromopurine with sodium sulfide in aqueous solvent or with hydrogen sulfide in a basic organic solvent, with an epoxide of the formula

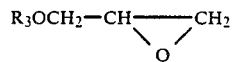

wherein $R_3$ is as defined above.

In this case the reaction is carried out in the presence of a polar, protic or aprotic, organic solvent, such as alcohols, dimethylformamide, dimethylsulfoxide etc. preferably in the presence of a basic catalyst typically selected from the group consisting of tertiary hindered amines such as trialkylamines, 2,6-lutidine, pyridine, etc.

The epoxide, which might be employed in equimolar amount to the purine or nucleoside substrate, is generally employed in a slight excess (ranging between 10 and 50% by mole). The reaction is preferably carried out at a temperature comprised between room temperature and 100° C. and preferably at the reflux temperature of a lower alkanol such as ethanol, isopropanol etc.

The reaction course is monitored by chromatography (TLC or HPLC) by checking the disappearance of the starting 8-mercaptopurine or nucleoside. The reaction is generally complete in a period of time ranging from 1 to 24 hours depending on the substrate and the catalyst possibly employed. At the end of the reaction, the crystallized product is recovered by filtration or by evaporating off the solvent, and purified by crystallization from suitable solvents or solvent mixtures or by chromatography.

Typically the obtained product is a mixture of two diastereoisomers having opposite configuration at the side-chain carbon atom bearing the hydroxy group.

Sometimes however repeated crystallizations may lead to a mixture richer and richer in one of the two isomers and even to optically pure isomers.

Alternatively, the methods which may be used to get the single pure isomers are the conventional methods of isomer separation such as for instance chromatography on chiral columns, formation of derivatives with optically active acids and separation of the thus obtained diastereoisomers, or stereo selective synthesis.

As for this last aspect, synthesis of the new products through reaction with a chiral epoxide is particularly suitable for a stereoselective synthesis. Other methods however can be devised, depending on the specifically desired compound, by any skilled chemist.

As for the starting materials, the 8-bromopurines or 8-bromonucleosides, are easily prepared from the corresponding commercially available purines or nucleosides through bromination with $Br_2$ in a buffered solution according to the method described by M. Ikehara et al. in Tetr. 26 (1970) page 4251. The compounds of formula R₃OCH₂—CH(OR')—CH₂XH, if unknown, are readily prepared by following the method known in chemistry for the synthesis of alkyl mercaptans (X=—S—) or glycols (X=—O—), while the epoxides are preferably prepared through reaction of epichlorohydrin with a compound R₃OH in the presence of an acceptor of the hydrogen chloride which forms during the reaction.

Finally compounds of formula I wherein $R_2$ is a hydrogen atom can be prepared either starting from the corresponding purine base bearing a hydrogen atom at the 9-position or removing the ribosyl group from the corresponding compound of formula I by acid hydrolysis with diluted hydrochloric acid. Likewise, some compounds of formula I may conveniently be prepared by chemical modification of other compounds still falling within formula I. As an example, compounds bearing a carboxy group as a substituent of $R_3$ may be prepared through basic hydrolysis of the corresponding compounds bearing an alkoxycarbonyl group and, in turn, they may be reacted with various alcohols or amines to give the corresponding esters or amides. In a further example the compound of formula I in which R is hydroxy and $R_1$ is hydrogen are conveniently prepared by nitrous acid treatment of the corresponding compounds of formula I wherein R is amino and $R_1$ is hydrogen.

The starting 8-mercaptonucleosides wherein the ribosyl hydroxy groups are derivatized are prepared from the corresponding 8-mercaptonucleosides through conventional esterification procedures.

When a compound of formula I is desired wherein only the primary hydroxy group is esterified or the primary hydroxy group is esterified differently from the two secondary hydroxy groups, it is necessary to block the two secondary hydroxy functions with a protecting group easily removable at the end of the reaction, preferably converting them into the corresponding acetonide, then derivatize the primary hydroxy group and finally set free the two secondary hydroxy groups which, if desired, may then be further reacted suitably.

The protection of the two secondary hydroxy groups of the ribosyl moiety may be carried out before or alternatively after introducing the bromine atom and replacing it with the —SH group, while derivatization of the primary hydroxy group is carried out after the mercapto group has been introduced and deprotection of the two seondary hydroxy groups may be carried out either before or after the reaction with the epoxide.

The following examples illustrate in detail some of the compounds of the invention and the process for their preparation, but in any case they must not be interpreted as a limitation of the scope of the invention.

EXAMPLE 1

8-{[[3-(4-ethoxycarbonyl)phenoxy-2-hydroxy]propyl]-thio}adenosine 8-mercapto-adenosine (45 g, 150 moles) is dissolved in ethyl alcohol (750 ml) and 1-(4-ethoxycarbonyl)-phenoxy-2,3-epoxypropane (36,8 g, 166 mmoles) and 2,6-lutidine (about 70 drops) are added to the obtained solution.

The reaction mixture is heated at reflux temperature for 2 hours, treated with charcoal and filtered when still hot. The reaction mixture is then stirred for 2 hours and then allowed to stand overnight. The crystalline product which precipitates is recovered, thoroughly washed with ethanol and then dried. The compound of the title (44 g) with the following characteristics is thus obtained:

m.p. 155°–57° C.;

$[\alpha]_D$ —43.55° (c=1 in MeOH);

two fusion endotherms at 145° C. and 158° C. in DSC.

Upon concentration of the mother liquor to small volume followed by the addition of ethyl ether to precipitate the compound, an additional crop (22 g) of the compound of the title is recovered.

EXAMPLE 2

6-amino-8-{[[3-(4-ethoxycarbonyl)phenoxy-2-hydroxy]propyl]-thio}purine

A mixture of 8-mercapto-adenine (5 g, 30 mmoles), 1-(4-ethoxycarbonyl)phenoxy-2,3-epoxypropane (10 g, 45 mmoles), dimethylformamide (100 ml) and pyridine (20 ml) is heated to 30°–40° C. under stirring for 24 hours, the cloudy solution is then filtered on celite, washed with ethanol and concentrated to dryness under vacuum. The residue is dissolved in ethanol and poured onto silica gel (150 g). The solvent is evaporated off and the residue is taken up in ethyl acetate (300 ml) and heated at reflux temperature. The reaction mixture is then allowed to cool and filtered and the solid on filter is treated as above once again. The residue is then crystallized from ethanol (350 ml) and ethyl acetate (100 ml) yielding 4.6 g of the compound of the title with m.p. 200°–201° C. By concentrating to dryness the filtrate, further 0.99 g of the compound of the title (m.p. 200°–1° C.) crystallize out.

EXAMPLE 3

6-amino-8-{[[3-(4-carboxy)phenoxy-2-hydroxy/-propyl/thio}purine

A mixture of 8-mercapto-adenine (5.22 g, 31.2 mmoles), 1-(4-ethoxycarbonyl)phenoxy-2,3-epoxypropane (7.63 g, 34.3 mmoles), pyridine (75 ml) and dimethylformamide (75 ml) is heated to 35° C. under stirring for 24 hours, then the solvent is evaporated off under vacuum, the residue is dissolved in boiling ethanol (1800 ml) and percolated through a silica-gel column (150 g).

The solvent is then evaporated off and the residue is extracted with hot ethyl acetate. The remaining residue is then triturated with a solution of potassium hydroxide (62.5 mmoles) in water (100 ml). After one night at room temperature, the mixture is treated with charcoal and filtered. The desired product is precipitated from the clear solution by the addition of acetic acid up to pH 4.5, recovered by filtration, dried and crystallized from dimethylformamide (300 ml) and ethanol (100 ml) yielding 2.96 g with m.p. 246°–248° C.

EXAMPLE 4

8-{[[3-(4-ethoxycarbonyl)phenoxy-2-hydroxy]propyl]-thio}guanosine 8-mercapto-guanosine(3.6 g, 11.4 mmoles) is added to anhydrous pyridine (100 ml) and 1-(4-ethoxycarbonyl)-phenoxy-2-epoxy-propane (3.8 g, 17.1 mmoles) is then added to the obtained solution. The reaction mixture is heated to 30° C. under stirring for 12 hours, then pyridine is evaporated off under vacuum and the oily residue is dissolved in ethanol (about 30 ml). Water (100 ml) is added and the mixture is extracted with ethyl acetate (3×50 ml). From the aqueous phase a white precipitate crystallizes out (0.4 g) and from the mother liquor additional 1.4 g of the compound of the title are recovered. The two crops are combined and dissolved in a boiling mixture water/ethyl alcohol 1/1 (110 ml). The solution is then treated with charcoal for ten minutes and then filtered. The clear solution thus obtained is allowed to stand for 4 days and the precipitate which crystallizes out is recovered by filtration, washed with water and dried yielding the compound of the title (1.14 g) with the following characteristics:

m.p. 130°–40° C.;

$[\alpha]_D^{30} = -29.6°$ (c = 1 in MeOH).

EXAMPLE 5

8-{[[3-(4-carboxy)phenoxy-2-hydroxy]propyl]thio}adenosine 1-(4-carboxy)phenoxy-2,3-epoxypropane (3.56 g, 18.3 mmoles) and 2,6-lutidine (27.4 mmoles) are added to a solution of 8-mercapto-adenosine (5.48 g, 18.3 mmoles) in ethanol (185 ml) and the reaction mixture is heated at reflux temperature for 1 hour and then treated with charcoal for 10 minutes.

After filtration, the solution is concentrated to half volume and white crystals are precipitated by friction. The precipitate is recovered, washed with ethanol and dried under vacuum yielding 5.5 g of the compound of the title with m.p. 188°–90° C. and $R_f$ 0.53 (acetone/acetic acid 95/5); $[\alpha]_D^{25} -47.5°$ (c = 1 dimethylformamide).

EXAMPLE 6

8-{[2-hydroxy-3-phenoxy-propyl]thio}adenosine

A mixture of 1-phenoxy-2,3-epoxypropane (7.3 g, 48.6 mmoles), 8-mercaptoadenosine (11.5 g, 38.4 mmoles), 2,6 lutidine (about 20 drops) and ethanol (300 ml) is heated at reflux temperature for 1 hour, then it is concentrated to a small volume and ethyl ether is added to precipitate the compound of the title as a raw product. The precipitate is recovered by filtration, washed with ether and dried, dissolved in boiling ethanol, added to an equal amount (by weight) of silica gel and concentrated to dryness. The obtained residue is charged on a silica gel (120 g) column prepared in ethyl acetate and developed with an ethylacetate/ethanol 9/1 mixture. Fractions, containing only the end product, are combined and crystallized from dichloroethane/ethanol 9/1 yielding 6.5 g of the compound of the title. M.p. 100°–110° C. Fusion endotherm at 105° C. in DSC and $[\alpha]_D^{30} -48.23°$ (c = 1, CH$_3$OH).

EXAMPLE 7

8-{[[3-(4-chloro-phenoxy-2-hydroxy]propyl]thio}adenosine 8-mercapto-adenosine (6.0 g, 20 mmoles), 1-(4-chloro)phenoxy-2,3-epoxypropane (3.7 g, 20 mmoles) and 2,6 lutidine (10 drops) are sequentially added to 100 ml of ethanol and the obtained reaction mixture is heated at reflux temperature for 1 hour. Additional 1-(4-chloro)phenoxy-2,3-epoxypropane (0.74 g, 4 mmoles) is then added and the mixture is refluxed for an additional hour. The obtained solution is filtered, cooled to room temperature and allowed to stand at room temperature overnight. The precipitate is recovered by filtration, washed with a small amount of ethanol and dried yielding 5.7 g of the compound of the title with m.p. 162°–64° C. and $[\alpha]_D^{30} -48.23°$ (c = 1 in methanol).

EXAMPLE 8

8-{[[3-(4-(2-methylpropoxycarbonyl)phenoxy)-2-hydroxy]propyl]thio}adenosine

A mixture of 8-mercapto-adenosine (33.5 g, 111.9 mmoles), 1-[4-(2-methylpropoxycarbonyl)phenoxy]-2,3-epoxypropane (33.6 g, 134.3 mmoles), ethanol (600 ml) and 2,6-lutidine (≃70 drops) is heated at reflux temperature for 90 minutes. The hot solution is then filtered and the clear solution is kept under mild stirring at room temperature.

After 3 hours the precipitate which forms is recovered by filtration, washed with ethanol followed by a small amount of ethyl ether and then dried under vacuum yielding 23.5 g of the compound of the title characterized by m.p. 166°–68° C. and $[\alpha]_D^{20} -29.4°$ (c = 1 MeOH) having an isomer ratio (as determined by 300 MHz NMR) of 70/30.

The mother liquor is concentrated to a small volume (about 150 ml) and ethyl ether (100 ml) is added thereto in order to complete precipitation. The precipitate is recovered by filtration, washed with ethyl ether and dried giving 25 g of the compound of the title with m.p. 161°–64° C. This product is dissolved in absolute ethanol (750 ml) and silica gel (50 g) is added to the obtained solution. The solvent is then evaporated off under vacuum and the residue is charged on a silica gel (300 g) column prepared in ethyl acetate. The fractions which, tested in TLC, are single-spot, are combined and concentrated to a small volume. The precipitate which forms is filtered, washed with ethyl acetate and dried under vacuum at 40° C. yielding 16 g of the compound of the title characterized by m.p. 168°–70° C. and $[\alpha]_D^{20} -52.62$ (c = 1 MeOH), having an isomer ratio of 30/70.

Starting from the compound with $[\alpha]_D^{20} -29.4°$ (23.5 g) and further crystallizing it from ethanol, a compound with $[\alpha]_D^{20} -14.92°$ (c = 1 MeOH) (12 g) is obtained, and further crystallizing this last compound still from ethanol, a compound with $[\alpha]_D^{20} -13.86°$ (c = 1 MeOH) (8 g) is obtained having an isomer ratio of 92/8 (R/S).

On the basis of the preparation of example 22, the major isomer (92%) is assigned the R configuration.

EXAMPLE 9

8-{[[3-(4-aminocarbonyl)phenoxy-2-hydroxy]propyl]thio}adenosine

A mixture of 8-mercapto-adenosine (5.8 g, 19.37 mmoles), 1-(4-aminocarbonyl)phenoxy-2,3-epoxy-propane (5.2 g, 26.9 mmoles), ethanol (200 ml) and 2,6-lutidine (20 drops) is heated at reflux temperature for 1 hours, then it is allowed to cool and ethyl ether is added to complete precipitation. The precipitate is recovered by filtration washed with ethyl ether and purified by chromatography on a silica gel column sequentially eluting with ethyl acetate, ethyl acetate/ethanol 9/1, and ethyl acetate/ethanol 1/1. Single-spot fractions are combined, concentrated to dryness, crystallized from ethanol and dried under vacuum at 120° C. for 18 hours yielding 2.9 g of the compound of the title with m.p. 175°–78° C. and $[\alpha]_D^{30} -40.54°$ (c = 1 MeOH).

EXAMPLE 10

8-{[[3-(4-N,N-diethylaminocarbonyl)phenoxy-2-hydroxy]propyl]thio}adenosine

A mixture of 8-mercapto-adenosine (3.5 g, 11.7 mmoles), 1-(4-N,N-diethylaminocarbonyl)phenoxy-2,3-epoxy-propane (4.0 g, 16 mmoles), ethanol (60 ml) and 2,6-lutidine (10 drops) is heated at reflux temperature for 1 hour. The mixture is then concentrated to half volume and ethyl ether is added to complete precipitation. The precipitate is recovered by filtration, washed with ether and purified by silica gel column chromatography eluting with an ethyl acetate/ethanol 9/1 mixture. Fractions containing only the desired end product are combined, concentrated to dryness, taken up in ethanol (50 ml) and added dropwise to ethyl ether (500 ml). The obtained precipitate is recovered, washed with ether and dried under vacuum yielding 3.25 g of the compound of the title with m.p.≃110° C., R$_f$0.27 Si.O$_2$ (ethyl acetate/ethanol 75/25) $[\alpha]_D^{30}-39.93°$ (c=1 MeOH).

EXAMPLE 11

8-{[[3-(2-ethoxycarbonyl)phenoxy-2-hydroxy]propyl]-thio}adenosine

A reaction mixture containing 8-mercapto-adenosine (4.7 g, 15.7 mmoles), 1-(2-ethoxycarbonyl)phenoxy-2,3-epoxy-propane (4.5 g, 20.2 mmoles), ethanol (80 ml) and 2,6-lutidine (10 drops) is heated at reflux temperature for 1 hour, then it is concentrated to half volume and poured into 10 volumes of ethyl ether. The precipitate is recovered, air dried and purified by silica gel column chromatography eluting with an ethyl acetate/ethanol 9/1 mixture. The precipitate which is obtained by combing the single spot fractions, concentrating them to dryness, taking up the residue in ethanol and adding ethyl ether, is recovered by filtration and dried under vacuum at 40°–50° C. yielding 5.6 g of the compound of the title with m.p. 95°–100° C. and $[\alpha]_D^{30}-41.79°$ (c=1 MeOH).

EXAMPLE 12

8-{[[3-(3-ethoxycarbonyl)phenoxy-2-hydroxy]propyl]-thio}adenosine 1-(3-ethoxycarbonyl)phenoxy-2,3-epoxy-propane (10.6 g, 47.7 mmoles) and 2,6-lutidine (20 drops) are added to a suspension of 8-mercapto-adenosine (12.8 g, 42.7 mmoles) in absolute ethanol (200 ml) and the obtained mixture is heated at reflux temperature for 80 minutes.

Further 10 g of the epoxide (4.5 mmoles) are added and the reaction mixture is refluxed for additional 15 minutes. The mixture is then concentrated to a small volume and poured into excess ethyl ether (500 ml). The precipitate is recovered, dried and purified by silica gel column chromatography as described in the preceding example yielding 8.5 g of the compound of the title with m.p.≃100° C. and $[\alpha]_D^{30}-39.84°$ (c=1, MeOH).

EXAMPLE 13

8-{[[3-(4-ethoxycarbonyl)phenoxy-2-hydroxy]propyl-]oxy}adenosine

The reaction is carried out under nitrogen atmosphere.

A solution of 3-(4-ethoxycarbonyl)phenoxy-2-(2-tetrahydropyranyl)oxy-propanol (4.95 g, 15.3 mmoles) in dimethylformamide (15 ml) is added to a suspension of oily 60% NaH (0.612 g, 15.3 mmoles) in anhydrous dimethylformamide (35 ml) at room temperature. After 10 minutes 8-bromo-N-[(dimethylamino)methylene]-2',3'-0-isopropylidene-5'-0-tetrahydropyranyl-adenosine (7 g, 13.3 mmoles) is added thereto and the reaction mixture is kept at room temperature for 1 hour and then heated to 50° C. After 2 hours at 50° C., the reaction mixture is allowed to cool and then poured into a stirred solution of NaH$_2$PO$_4$ (10 g) in water (150 ml) and ethyl acetate (250 ml). The two phases are separated and the aqueous one is extracted with ethyl acetate (100 ml). The organic phases are washed with water (2×100 ml), dried over Na$_2$SO$_4$ and concentrated to dryness. The residue (10 g) is purified by flash chromatography on silica gel (300 g) eluting with ethyl acetate (1500 ml) first and with ethyl acetate containing 10% acetone (3l) then.

The useful fractions are combined and concentrated to dryness yielding 8 g of N-[(dimethylamino)methylene]-2', 3'-O-isopropylidene-5'-0-tetrahydropyranyl-8-{[[3-(4-ethoxycarbonyl)phenoxy-2-(2-tetrahydropyranyl)oxy]propyl]oxy}adenosine as a viscous oil.

5 g of this product (6.51 mmoles) are dissolved in ethanol 1N H$_2$SO$_4$ (50 ml) and after 1 hour aqueous 1N H$_2$SO$_4$ (50 ml) is added. The reaction, monitored by HPLC, is complete in 24 hours. The pH is then neutralized by the addition of a saturated KHCO$_3$ solution, most ethanol is removed under vacuum and the mixture is extracted with ethyl acetate (300 ml+2×150 ml). The organic phase is dried over Na$_2$SO$_4$ and concentrated to dryness. The residue, dissolved in acetone (50 ml), is adsorbed on silica gel (50 g) and charged on a silica gel (100 g) column prepared in ethyl acetate/ethanol 99/1. The column is eluted with ethyl acetate/ethanol mixtures in volume ratio ranging from 99/1 to 85/15 yielding 3 fractions, which contain the compound of the title in percentage varying from 72 to 85%.

Silanized silica gel RP 8 (25 g) is added to a stirred solution of 6 g of the above raw product in 95% ethanol (45 ml).

The solvent is removed at 40° C. under stirring and the obtained residue is applied to a silanized silica gel RP 8 column prepared in 0.005M phosphate buffer pH 7.4/95% ethanol 7/3, developed under overatmospheric pressure with 0.005M phosphate buffer pH 7.4/95% ethanol 7%3 (2000 ml) followed by 0.005M phosphate buffer pH 7.4/95% ethanol 65/35 (3500 ml) and collecting 100-ml fractions.

Fractions containing only the desired product are combined, concentrated at 40° C. under vacuum to a small volume, salted with NaCl and extracted with ethyl acetate (500 ml+3×250 ml). The organic extracts are combined, dried over Na$_2$SO$_4$ and concentrated to dryness giving the compound of the title as a white solid which is crystallized from ethanol. Yield: 2.1 g. M.p. 166°68° C.

$[\alpha]_D^{20}-36.72°$ (c=0.964 in methanol). UV$_{MeOH}$: $\lambda_{max}$256 nm ($\epsilon$38445).

EXAMPLE 14

8-{[[2-hydroxy-3-(4-(3-pyridyl)-methoxycarbonyl)-phenoxy]propyl]thio}-adenosine (A) Nicotinyl alcohol (2.42 g, 22.2 mmole), dimethylaminopyridine (360 mg) and dicyclohexylcarbodiimide (4.6 g, 22.3 mmole) are added to a solution of 1-(4-carboxy)phenoxy-2,3-epoxy-propane (4.3 g, 22.1 mmole) in anhydrous dimethylformamide (45 ml). The obtained reaction mixture is allowed to stand overnight and the resulting suspension is then poured into ethyl ether (200 ml) and washed with water (5×50 ml). The clear solution is evaporated to give an oily product.

(B) Said product is added to a suspension of 8-mercapto-adenosine (3.5 g, 11.7 mmole) and 2,6-lutidine (5 drops) in ethanol (50 ml). The suspension is heated at reflux temperature for 1 hour, then it is filtered and the filtrate is concentrated to a small volume (about 15 ml) and poured into ethyl ether (200 ml). The resulting precipitate is collected by filtration, dried under vacuum and triturated with an equal amount of silica gel. The obtained mixture is applied to a silica gel column prepared in ethyl acetate and developed with a mixture ethyl acetate/ethanol 9/1. Fractions containing the obtained product are combined and concentrated to a small volume.

Ethyl ether is added thereto and the precipitate which forms is recovered by filtration and dissolved in boiling ethanol (200 ml). The solution is treated with charcoal for 5 minutes then filtered. The compound of the title which crystallizes out, is then collected by filtration and dried under vacuum yielding 2.7 g of a white crystalline product with m.p. 115°–18° C.; $[\alpha]_D^{20} -31.26°$ (c=0.5 in methanol).

EXAMPLE 15

8-{[2-hydroxy-3-[(4-dodecyloxycarbonyl)phenoxy]-propyl]thio}adenosine

A suspension of 8-mercapto-adenosine (4.9 g, 16.4 mmole), 1-(4-dodecyloxycarbonyl)phenoxy-2,3-epoxy-propane (5.4 g, 14,9 mmole), 2,6-lutidine (5 drops) and absolute ethanol (100 ml) is heated at reflux temperature for a couple of hours, then the obtained solution is allowed to cool slowly under stirring. The white crystalline precipitate which forms is recovered by filtration, washed with ethanol (about 25 ml) and dried under vacuum yielding 6.2 g of the compound of the title with m.p. 163°–65° C.; $[\alpha]_D^{20} -39.98°$ (c=1 in dimethylformamide).

EXAMPLE 16

8-{[2-hydroxy-3-[(4-2-acetylamino)ethoxycarbonyl)-phenoxy]propyl]thio}adenosine

A mixture of 1-(4-(2-acetylamino)ethoxycarbonyl)-phenoxy-2,3-epoxy-propane (5.3 g, 18.9 mmole), 8-mercaptoadenosine (6.9 g, 23 mmole) and 2,6-lutidine (10 drops) in absolute ethanol (120 ml) is refluxed for 1 hour, then it is concentrated to a small volume (about 30 ml) and poured into ethyl ether (500 ml) giving a bulkyl precipiate which is recovered by filtration and washed with ethyl ether. The raw product thus obtained is dried under vacuum and purified by flash chromatography on a silica gel 60 column prepared in ethyl acetate/ethanol 75/25 and developed with the same solvent system collecting 250 ml fractions. Fractions 14 to 20 are combined, dried under vacuum and crystallized from ethanol yielding 4.2 g of the compound of the title with m.p. 124°–26° C. and $[\alpha]_D^{20} -46.57°$ (c=1 in methanol).

EXAMPLE 17

8-{[[2-hydroxy-3-[(4-ethoxycarbonyl-2,6-dimethoxy)-phenoxy]]propyl]thio}adenosine A suspension of 8-mercapto-adenosine (9.0 g, 30 mmole) and 1-(4-ethoxycarbonyl-2,6-dimethoxy)-phenoxy-2,3-epoxy-propane (11.86 g, 42 mmole) in ethanol (150 ml) and 2,6-lutidine (15 drops) is heated at reflux temperature for 2 hours, then allowed to cool to room temperature, concentrated to a small volume (about 50 ml) and poured into stirred ethyl ether (500 ml). The white precipitate which forms is collected by filtration, washed with ethyl ether and air-dried yielding 14.5 g of a raw product. An ethanol solution of said raw product is added to silica gel (22 g) and the obtained suspension is concentrated to dryness. The residue is dissolved in ethanol (28 ml) and poured into ethyl ether (500 ml). A white precipitate forms which is recovered by filtration, washed with ether (100 ml) and dried under vacuum at 40° C. yielding 5.5 g of the compound of the title with m.p. 102°–04° C. and $[\alpha]_D^{20} -49.26°$ (c=0.5 in methanol).

EXAMPLE 18

8-{[2-hydroxy-3-[(4-ethoxycarbonyl)phenoxy]propyl]-thio}inosine

A solution of sodium nitrite (24 g, 0.347 mole) in water (50 ml) is added to a solution of 8-{[[3-(4-ethoxycarbonyl)phenoxy-2-hydroxy]propyl]thio}-adenosine (10 g, 19.2 mmol) in acetic acid (100 ml) and water (200 ml) keeping the temperature between 0° C. and 10° C. After 1 hour, the reaction mixture is allowed to warm to room temperature and sodium bicarbonate is added up to neutral reaction. The obtained product is extracted with a mixture ethyl acetate/n-butanol 7/3 (1000 ml). The organic extract is then dried over $Na_2SO_4$ and concentrated to dryness. The obtained residue is purified by flash chromatography over silica gel eluting with ethyl acetate/ethanol 9/1 first and then with ethyl acetate/ethanol 85/15. Fractions containing the desired product are combined and concentrated to dryness yielding 8.2 g of the compound of the title as a raw product. This residue is dissolved in a mixture methylene chloride/n-butanol 7/3 (1000 ml) and extracted with iced 5% aqueous ammonia. The aqueous phase is then brought to to pH 6 by the addition of 10% $H_2SO_4$ and extracted with ethyl acetate/n-butanol 7/3 (100 ml). The organic phase id dried over $Na_2SO_4$ and concentrated to dryness to give a residue which is crystallized from hot isopropanol by the slow addition of ethyl ether yielding 5.3 g of the compound of the title.

$[\alpha]_d^{20} -35.17°$ (c=1.01 in methanol); $UV_{MeOH}\lambda_{max}$ 258 nm (ε31227).

EXAMPLE 19

8-{[[2-hydroxy-3-[2-(5-ethoxycarbonyl)pyridyloxy]]-propyl]thio}adenosine

A mixture of 1-[2-(5-ethoxycarbonyl)pyridyloxy]-2,3-epoxy-propane (5.2 g, 23 mmoles) and 8-mercapto-adenosine (6.9 g, 23 mmoles) in ethanol (130 ml) is heated at reflux temperature for 45 minutes, then it is cooled to room temperature and concentrated to a small volume. Ethyl ether is added thereto and the solid which precipitates is recovered by filtration, washed with ethyl ether and air-dried. The raw product thus obtained is purified by silica gel column chromatography eluting with ethyl acetate/ethanol 75/25 and crystallized from ethanol by the addition of ethyl ether.

Yield: 3.0 g $[\alpha]_D^{20} -86.38°$ (c=1 in methanol). $UV_{MeOH}\lambda_{max}$ 267 nm (ε32511).

EXAMPLE 20

8-{[2-hydroxy-3-[(4-ethoxycarbonyl)phenoxy]propyl]-thio}adenosine 2′,3′5′-triacetate The compound of the title is prepared by following substantially the same procedure as in Example 1 but starting from 8-mercapto-adenosine 2′,3′,5′-triacetate. M.p. 66°–70° C.; $[\alpha]_D^{20} -7.94°$ (c=1 in methanol).

$UV_{MeOH}\lambda_{max}$ 272 nm (ε26144) and 279.8 nm (ε28989).

EXAMPLE 21

8-{[2-hydroxy-3-[(4-ethoxycarbonyl)phenoxy]propyl]-thio}adenosine 5′-(3,4,5-trimethoxy)benzoate A solution of 8-mercapto-2′,3′-O-isopropylidene-adenosine 5′-(3,4,5-trimethoxy)benzoate (1 g, 1.9 mmoles), 1-(4-ethoxycarbonyl)phenoxy-2,3-epoxy-propane (0.5 g, 2.2 mmoles) and 2,6-lutidine (3 drops) in absolute ethanol (20 ml) is refluxed for 90 minutes. The mixture is then concentrated to dryness and the obtained residue is purified by silica gel column chromatography eluting with methylene chloride and methylene chloride/ethanol mixtures with increasing percentages of ethanol up to 97/3 yielding 1.1 g of 8-{[2-hydroxy-3-[(4-ethoxycarbonyl)phenoxy]propyl]thio}-2',3'-O-isopropylidene-adenosine 5'-(3,4,5-trimethoxy)-benzoate.

A mixture of the above intermediate product (10 g) in ethanol 1N $H_2SO_4$ (100 ml) is stirred at room temperature for 48 hours, neutralized with $NaHCO_3$ and extracted with ethyl acetate. The organic phase is dried over $Na_2SO_4$ aand concentrated to dryness giving a residue which is purified by silica gel column chromatography eluting with ethyl acetate, nd then crystallized from ethanol by the addition of ethyl ether. Yield: 3.7 g $[\alpha]_D^{20} -29.44°$ (c=1.019 in methanol). Elemental analysis: calculated for $C_{32}H_{37}O_{12}N_5SC$ 53.7%; H 5.21%; N 9.78%; found C 53.06%; H 5.29%; N 9.77%

EXAMPLE 22

8-}[[2-(S)-hydroxy-3-(4-isobutyloxycarbonyl)phenoxy]-propyl]thio}adenosine

A mixture of 8-mercapto-adenosine (5.54 g, 18.5 mmoles), 1-/4-(2-methylpropoxycarbonyl)phenoxy-2,3-(2R)-epoxy-propane (5.45 g, 21.77 mmoles) and 2,6-lutidine (10 drops) in ethanol (100 ml) is heated at reflux temperature under stirring for 90 minutes. Additional 350 mg (1.4 mmoles) of the epoxide are added to the reaction mixture and reflux is continued for further 45 minutes. The mixture is then filtered and allowed to stand overnight. The precipitate which forms is recovered by filtration and taken up in warm ethanol. Silica gel (15 g) is added to the obtained solution, the suspension is evaporated under vacuum and the residue is applied to a silica gel column prepared in ethyl acetate and developed with a mixture ethyl acetate/ethanol 9/1 applying a slightly overatmospheric pressure.

Fractions containing only the reaction product are combined and evaporated to a small volume. Ethyl ether is added and the obtained precipitate is recovered by filtration, washed with ethyl ether and dissolved in boiling ethanol (100 ml). The solution is filtered and allowed to cool to room temperature under mild stirring. The precipitate is separated, washed with ethanol (50 ml) and dried under vacuum at 50° C. yielding 4.2 g of the compound of the title. M.p. 166°–68° C.;

$[\alpha]_D^{20} -76.05°$ (c=1 in methanol).

By following substantially the procedures described in the general descriptive portion and in the preceding examples, the following compounds are prepared:

8-{[[3-(4-methoxycarbonyl)phenoxy-2-hydroxy]-propyl]thio}-adenosine

8-{[[3-(4-(2-methoxyethoxy)carbonyl)phenoxy-2-hydroxy]propyl]thio}adenosine

8-{[[3-(4-isopropoxy-carbonyl)phenoxy-2-hydroxy]-propyl]thio}adenosine

8-{[[3-(4-(2-ethoxyethoxy)carbonyl)phenoxy-2-hydroxy]propyl]thio}adenosine

8-{[[3-(4-hexyloxycarbonyl)phenoxy-2-hydroxy]-propyl]thio}adenosine

8-{[[3-(4-heptyloxycarbonyl)phenoxy-2-hydroxy]-propyl]thio}adenosine

8-{[[3-(4-benzyloxycarbonyl)phenoxy-2-hydroxy]-propyl]thio}adenosine

8-{[[3-4-(2,3-dihydroxypropoxy)carbonyl)phenoxy-2-hydroxy]propyl]thio}adenosine

8-{[[3-4-(2-N,N-dimethylaminoethoxy)carbonyl]-phenoxy-2-hydroxy propyl]thio}adenosine 8-{[[3-(4-ethoxycarnonyl-2-methoxy)phenoxy-2-hydroxy]propyl]thio}adenosine 8-{[[3-(4-nitro)phenoxy-2-hydroxy]propyl]thio adenosine 8-{[[3-(4-ethoxycarbonyl-3-methoxyl)phenoxy-2-hydroxy]propyl]thio}adenosine 8-{[[3-(4-ethoxycarbonyl-2-hydroxy)phenoxy-2-hydroxy]propyl]thio}adenosine 8-{[[3-(4-ethoxycarbonyl-3-hydroxy)phenoxy-2-hydroxy]propyl]thio}adenosine 8-{[[3-(2-chloro-4-ethoxycarbonyl)phenoxy-2-hydroxy]propyl]thio}adenosine 8-{[[3-(3-chloro-4-ethoxycarbonyl)phenoxy-2-hydroxy]propyl]thio}adenosine 8-{[[3-(2,6-dichloro-4-ethoxycarbonyl)phenoxy-2-hydroxy]propyl]thio}adenosine 8-{[[3-(3,5-dichloro-4-ethoxycarbonyl)phenoxy-2-hydroxy]propyl]thio}adenosine 8-{[[3-(2-amino-4-ethoxycarbonyl)phenoxy-2-hydroxy]propyl]thio}adenosine 8-{[[3-(3-amino-4-ethoxycarbonyl)phenoxy-2-hydroxy]propyl]thio}adenosine 8-{[[3-(2,6-diamino-4-ethoxycarbonyl)phenoxy-2-hydroxy]propyl]thio}adenosine 8-{[[3-(3,5-diamino-4-ethoxycarbonyl)phenoxy-2-hydroxy]propyl]thio adenosine 8-{[[3-(2-N,N-dimethylamino-4-ethoxycarbonyl)-phenoxy-2-hydroxy]propyl]thio}adenosine 8-{[[3-(3-N,N-diethylamino-4-ethoxycarbonyl)-phenoxy-2-hydroxy]propyl]thio}adenosine 8-{[[3-(3-pyridyloxy)-2-hydroxy]propyl]thio}adenosine 8-{[[3-(2-ethoxycarbonyl-3-pyridyloxy)-2-hydroxy]-propyl]thio}adenosine 8-{[[3-(3-nitro-4-ethoxycarbonyl)phenoxy-2-hydroxy]-propyl]thio}adenosine 8-{[[3-(3-nitrophenoxy)-2-hydroxy]propyl]thio}adenosine 8-{[[3-(2-nitrophenoxy)-2-hydroxy]propyl]thio}adenosine 8-{[[3-(4-ethoxycarbonyl)phenoxy-2-hydroxy]propyl]-thio}adenosine 5'-acetate 8-{[[3-(4-ethoxycarbonyl)phenoxy-2-hydroxy]propyl]-thio}adenosine 5'-benzoate 8-{[[3-(4-ethoxycarbonyl)phenoxy-2-hydroxy]propyl]-thio}adenosine 5'-isobutyrate 8-{[[3-(5-ethoxycarbonyl)phenoxy-2-hydroxy]propyl]-thio}adenosine 5'-nicotinate 8-{[[3-(4-ethoxycarbonyl)phenoxy-2-hydroxy]propyl]-thio}adenosine 5'-phosphate 8-{[[3-(4-ethoxycarbonyl)phenoxy-2-hydroxy]propyl]-thio}adenosine 5'-carbamate 8-{[[3-(4-ethoxycarbonyl)phenoxy-2-hydroxy]propyl]-thio}adenosine 2',3',5'-tricarbamate 8-{[[3-(4-ethoxycarbonyl)phenoxy-2-hydroxy]propyl]-thio}adenosine 2',3',5'-triisobutyrate 8-{[[3-(4-ethoxycarbonyl)phenoxy-2-hydroxy]propyl]-thio}adenosine 5'-nicotinate 2',3'-diacetate 8-{[[3-(4-ethoxycarbonyl)phenoxy-2-hydroxy]propyl]-thio}adenosine 5'-nicotinate 2',3'-dicarbamate 8-{[[3-(4-ethoxycarbonyl)phenoxy-2-hydroxy]propyl]-thio}adenosine 5'-nicotinate 2',3'-diisobutyrate 6-amino-8-{[[3-(4-methoxycarbonyl)phenoxy-2-hydroxy]propyl]thio}purine 6-amino-8-{[[3-(4-isopropoxycarbonyl)phenoxy-2-hydroxy]propyl]thio}purine 6-amino-8-{[[3-(3-pyridyloxy)-2-hydroxy]propyl]thio}purine 8-{[[3-(4-isopropoxycarbonyl)phenoxy-2-hydroxy]-propyl]oxy}adenosine 6-amino-8-{[[3-(4-ethoxycarbonyl)phenoxy-2-hdroxy]-propyl]oxy}purine 6-amino-8-{[[3-(4-methoxycarbonyl)phenoxy-2-hydroxy]propyl]oxy}purine 8-{[[3-(4-methoxycarbonyl)phenoxy-2-hydroxy]propyl]oxy}adenosine 8-{[[3-(3-pyridyloxy)-2-hydroxy]propyl]oxy}adenosine Preparation of the starting materials (A) 1-(4-ethoxycarbonyl)phenoxy-2,3-epoxy-propane A mixture of 4-hydroxy-benzoic acid ethyl ester (58.2 g, 0.35 mole), epichlorohydrin (72.39 g, 0.78 mole) and fine powdered potassium carbonate dried at 120° C. under vacuum (0.55 mole) in methyl ethyl ketone (750 ml) is heated at reflux temperature under stirring for 9 hours. The suspension is then taken up in ethyl ether (2000 ml) and water (150 ml), the two phases are separated and the organic phase is washed with water ($2 \times 100$ ml), dried and concentrated to dryness. The obtained oil dissolved in methylene chloride is percolated on silica gel (500 g) yielding 62 g of the desired product with m.p. 54°–55° C. (from ethyl ether).

(B) 1-(4-carboxy)phenoxy-2,3-epoxy-propane

1N NaOH (500 ml, 50 mmoles) is added to a solution of 1-(4-ethoxy-carbonyl)phenoxy-2,3-epoxy-propane (12.35 g, 55.5 mmoles) in dioxane (1000 ml) and the reaction mixture is allowed to stand at room temperature for five days.

Dioxane is mostly evaporated off under vacuum and the mixture is then extracted with ethyl ether ($2 \times 50$ ml).

The aqueous phase is then brought to pH 4.5 with sodium phosphate monobasic and extracted with ethyl acetate ($3 \times 500$ ml). The organic extracts are dried over $Na_2SO_4$, ethyl acetate is evaporated off under vacuum and the residue is crystallized from ethanol/hexane yielding 5.6 of the compound of the title with m.p. 166°–68° C.

(C) 1-[4-(2-methylpropoxycarbonyl)phenoxy]-2,3-epoxy-propane

Finely powdered potassium carbonate previously dried at 120° C. for two days (116.25 g, 0.84 mole) and epichlorohydrin (85.8 g, 0.93 mole) are added to a solution of 4-hydroxybenzoic acid 2-methylpropyl ester (90 g, 0.463 mole) in methyl ethyl ketone (750 ml) and the reaction mixture is heated at reflux tmperature for about 10 hours.

An equal volume of ethyl ether and 200 ml of water are then added and the two phases are separated. The organic phase id dried and evaporated to give a thick oil which is purified by under vacuum distillation (1 mmHg) at 155° C., giving 87 g of the compound of the title.

(D) 1-[(4-N,N-diethylaminocarbonyl)phenoxy]-2,3-epoxy-propane

Epichlrohydrin (2.15 g, 23.2 mmoles) is added to a solution of N,N-diethyl 4-hydroxybenzamide (3.0 g, 15.5 mmoles) in 1N KOH (19 mmoles) and the obtained mixture is stirred at room temperature for 48 hours. The reaction mixture is then extracted with chloroform ($2 \times 50$ ml) and the organic phase is washed with water, dried and concentrated to dryness to give an oily product which is purified by dissolving it in chloroform (10 ml), percolating the obtained solution on silica gel (50 g) in chloroform and eluting with the same solvent, giving 2 g of the compound of the title as an oily product.

(E) 1-(2-ethoxycarbonyl)phenoxy-2,3-epoxy-propane

This product has been prepared by following substantially the same procedure as under item (A) but starting from 2-hydroxy-benzoic acid ethyl ester. Oily product purified by chromatography.

(F) 1-(3-ethoxycarbonyl)phenoxy-2,3-epoxy-propane

The compound of the title has been prepared by following the procedure described under item (A) but starting from 3-hydroxy-benzoic acid ethyl ester. Oily product with b.p. 155°–57° C./0.7 mmHg.

(G) 1-(4-chlorophenoxy)-2,3-epoxy-propane

This product has been prepared by following the procedure described under item (D) but starting from 4-chlorophenol.

Oily product with b.p. 95°–100° C./1 mmHg.

(H) 1-phenoxy-2,3-epoxy-propane.

The compound of the title has been prepared by following the procedure described under item (D) but starting from phenol.

(I) 1-(4-aminocarbonyl)phenoxy-2,3-epoxy-propane

The compound of the title has been prepared by following substantially the same procedure as in item (D) but starting from 4-hydroxybenzamide.

M.p. 138°–40° C.

(J) 3-(4-ethoxycarbonyl)phenoxy-2(2-tetrahydropyranyl)oxy-propanol (i) A vigorously stirred solution of 4-hydroxy-benzoic acid ethyl ester (25 g, 0.15 mole), benzyl 2,3-epoxypropyl ether (16.4 g, 0.1 mole), $K_2CO_3$ (10 g, 0.072 mole) and methyl ethyl ketone (100 ml) is heated at reflux temperature for 5 hours. The reaction mixture is then allowed to cool, filtered and concentrated to dryness under vacuum. The residue is taken up in ethyl ether (250 ml) and washed with water (100 ml), 10% NaOH (200 ml), 5% $NaH_2PO_4$, and water. Then the ether solution is dried over $Na_2SO_4$ and concentrated to dryness under vacuum yielding 22 g of 1-benzyloxy-2-hydroxy-3-[(4-ethoxycarbonyl)phenoxy]propane as a thick colorless oil.

(ii) The product thus obtained (0.0665 mole) is added at room temperature to a stirred mixture of dihydropyran (8.47 g, 0.1 mole) and pyridinium p-toluensulfonate (1.8 g, 0.007 mole) in methylene chloride (270 ml).

The reaction mixture is allowed to stand for 16 hours, then it is washed with a saturated bicarbonate solution (100 ml) and with water (50 ml), dried over $Na_2SO_4$ and concentrated to dryness. The residue is purified by silica gel column chromatography. eluting with ethyl acetate/hexane 2/8. 1-Benzyloxy-2-(2-tetrahydropyranyl)oxy-3-[(4-ethoxycarbonyl)phenoxy]propane (25 g) is obtained as a colorless thick oil.

(iii) 9 g of this product (21.7 mmoles) are added to a mixture of 20% palladium hydroxide on carbon (1 g) in absolute ethanol (150 ml) and cyclohexene (70 ml) and the mixture is heated at reflux temperature for 1 hour.

The catalyst is then filtered off and the solution is concentrated to dryness under vacuum.

The residue (7.6 g) is chromatographed on silica gel (100 g) eluting with a mixture ethyl acetate/hexane 2/8 (750 ml) and then with ethyl acetate/hexane 3/7 (1000 ml). 4.53 g of the desired product are thus obtained.

(K) 1-(4-dodecyloxycarbonyl)phenoxy-2,3-epoxypropane

Dodecyl alcohol (18.6 g, 0.1 mole) and conc. $H_2SO_4$ (2 ml) are added to a suspension of 4-hydroxy-benzoic acid (16.6 g, 0.12 mole) in toluene (100 ml) and the reaction mixture is refluxed for 6 hours. After cooling to room temperature, the suspension is diluted with ethyl ether (2 volumes), washed with water (2×100 ml) and evaporated to give an oily residue which is taken up in ethyl ether (200 ml) and filtered under vacuum over celite.

The clear solution is washed with saturated aqueous sodium bicarbonate, dried over $Na_2SO_4$ and concentrated to yield an oily residue (about 25 g). This product is mixed with epichlorohydrin (18 g, 0.2 mole) and $K_2CO_3$ (25 g) in methyl ethyl ketone (250 ml) and the obtained mixture is refluxed for 5 hours, then allowed to stand overnight, diluted with ethyl ether (250 ml) and washed with water (2×100 ml). The ethyl ether solution is then dried over $Na_2SO_4$ and concentrated under vacuum to an oily residue which is applied to a silica gel column prepared in methylene chloride and developed with the same solvent. The fractions which contain the desired product are combined yielding 19 g of a raw product which is further purified by flash chromatography on a silica gel 60 column prepared in ethyl ether/hexane 40/60 and developed with the same solvent mixture collecting 200-ml fractions. Fractions 3 to 5 are combined and concentrated to dryness giving 13 g of the compound of the title as a pure product.

(L) 1-(4-2-acetylamino)ethoxycarbonyl)phenoxy-2,3-epoxy-propane

2-Acetylamino-ethanol (14.5 g, 140.6 mmoles) is added to a stirred solution of (4-dcarboxy)phenoxy-2,3-epoxy-propane (9.7 g, 49.95 mmoles) in anhydrous dimethylformamide (45 ml) and methylene chloride (350 ml) and stirring is prolonged for 2 hours. 4-Dimethylamino-pyridine (0.3 g) and dicyclohexylcarbodiimide (19.4 g, 94 mmoles) are then added thereto and the resulting mixture is stirred for 2 hours and then allowed to stand overnight. After filtering off the insoluble, the clear solution is concentrated to a small volume by evaporating off part of the dimethylformamide by azeotroping it with xylene, and purified by flash chromatography on a silica gel 60 column prepared in ethyl acetate and developed with the same solvent collecting 250 ml fractions. Fractions 10 to 15 are combined and concentrated to dryness yielding 5.4 of the compound of the title.

(M) 1-(4-ethoxycarbonyl-2,6-dimethoxy)phenoxy-2,3-epoxy-propane

A mixture of 4-hydroxy-3,5-dimethoxy-benzoic acid (40 g, 201.8 mmoles), conc. $H_2SO_4$ (7 ml) and ethanol (200 ml) is refluxed for 9 hours, then it is concentrated to a small volume and the residue is taken up in ethyl acetate. The ethyl acetate solution is washed carefully with water, dried over $Na_2SO_4$ and evaporated to yield an oily residue. Sodium (1.6 g, 69 mmoles) in ethanol (100 ml) is added to 15 g of said oily residue (about 69 mmoles) dissolved in ethanol. Toluene is then added and the azeotrope ethanol/toluene is removed by distillation giving a thick suspension of sodium (4-ethoxycarbonyl-2,6-dimethoxy)phenoxide in toluene. Epichlorohydrin (150 ml) is added thereto and the reaction mixture is refluxed for a couple of hours. Epichlorohydrin (about 50 ml) and toluene (about 100 ml) are then distilled off as an azeotrope and dimethylformamide (100 ml) is added.

After heating at reflux temperature for 1 hour, the reaction mixture is cooled to room temperature, diluted with ethyl ether (1000 ml), washed with water and evaporated to give an oily residue. This residue is purified by silica gel column chromatography sequentially eluting with ethyl acetate/methylene chloride 1/9 (1000 ml), ethyl acetate/methylene chloride 2/8 (500 ml), ethyl acetate (1000 ml). Fractions containing only the desired compound are combined and evaporated to give an oily colorless residue which solidifies on standing.

Yield: 14.59 g (N) 1-[2-(5-ethoxycarbonyl)pyridyloxy]-2,3-epoxy-propane

A solution of 5-chloro-nicotinic acid ethyl ester (3.08 g, 16.6 mmoles) and glycidol (1.26 g, 17 mmoles) in anhydrous dimethylformamide (40 ml) is added dropwise to a suspension of 60% NaH (0.68 g, 17 mmoles) in anhydrous dimethylformamide keeping the temperature at 0°–5° C. The reaction mixture is stirred at room temperature overnight, then it is poured into water (100 ml) and extracted with ethyl ether (2×100 ml). The combined organic extracts are dried over $Na_2SO_4$ and evaporated under vacuum to give an oily residue which solidifies on standing.

The starting 5-chloro-nicotinic acid ethyl ester in its turn is obtained from 5-hydroxy-nicotinic acid ethyl ester through reaction with $PCl_5/POCl_3$ according to conventional methods.

(O) 1-4-(2-methylpropoxy)carbonyl)phenoxy-2,3-(2R)-epoxy-propane 4-hydroxy-benzoic acid isobutyl ester (38 g, 195.6 mmoles) is slowly added to a stirred suspension of 60% NaH in oil (7.1 g, 177.5 mmoles) in anhydrous dimethylformamide (300 ml) keeping the temperature at 0°–5° C. Stirring is prolonged for 20 minutes, then a solution of 2,2-dimethyl-1,3-dioxolan-(4R)-4-methanol p-toluenesulfonate (46 g, 160.6 mmoles) in anhydrous dimethylformamide (100 ml) is added thereto in 10 minutes. The reaction mixture is heated to 130° C. for 1 hour, then cooled to room temperature and poured into crushed ice (700 g). The aqueous phase is extracted with ethyl ether (2×500 ml) and the organic extracts are combined, washed with 1N NaOH until the excess 4-hydroxy-benzoic acid isobutyl ester is removed and then with water up to neutral reaction. After drying the ether phase over $Na_2SO_4$, the solvent is distilled of leaving an oily residue which solidifies on standing (Yield: 47 g; $[\alpha]_D^{20} +6.47°$ (c=1 in methanol).

9.0 g of this product are dissolved in acetic acid (15 ml) and HBr in $CH_3COOH$ (13.9 ml of a 40% solution (d=1.46), 100 mmoles of HBr) is added dropwise to the obtained solution. After 90 minutes the reaction mixture is poured into water (300 ml) containing $NaHCO_3$ (70 g, about 830 mmoles) and ethyl ether (500 ml). The organic phase is separated, washed with water, dried over $Na_2SO_4$ and evaporated to dryness. The oily residue is chromatography eluting with hexane/ethyl acetate (Yield: 10.8 g). This product is dissolved in isobutanol and the obtained solution is gradually dripped into a solution of sodium (0.7 g, 30.4 mmoles) in isobutanol (110 ml). After 30 minutes the resulting suspension is poured into toluene (200 ml) and washed with 10% aqueous $NaH_2PO_4$ (100 ml) and then with water (2×50 ml), dried over $Na_2SO_4$ and evaporated to dryness under vacuum. The raw residue is dissolved in methylene chloride and applied to a silica gel column prepared in methylene chloride and developed with the same solvent (1000 ml). Fractions containing only the desired epoxyde are combined and concentrated to dryness yielding 6.2 g of the compound of the title as an oily product with $[\alpha]_D^{20} -9.45°$ (c=1 in methanol).

(P) 8-mercaptoadenosine; 8-mercaptoadenine; and 8-mercaptoguanosine—These known products have been prepared following the methods known in literature for their synthesis.

(Q) 8-bromo-N-[(dimethylamino)methylene]-2',3'-O-isopropylidene-5'-O-tetrahydropyranyl-adenosine (i) Dihydropyran (34.6 g, 0.41 mole) is added to a suspension of 2',3'-O-isopropylidene-8-bromoadenosine (79 g, 0.204 mole) and anhydrous p-toluenesulfonic acid (obtained from 35 g (0.197 mole) of monhydrate through azeotropic distillation from toluene) in ethyl acetate (1 liter).

After 90 minutes at room temperature the mixture is poured into a sodium carbonate (60 g) solution in water (600 ml) and the two phases are separated. The aqueous phase is extracted with ethyl acetate (200 ml) and the organic extract is dried over $Na_2SO_4$ and concentrated to 200 ml. Ethyl ether is added, after one night in refrigerator, the precipitate (44 g) is recovered by filtration. The mother liquors are concentrated to dryness and the obtained residue is purified by flash chromatography on silica gel (700 g) eluting with ethyl acetate/hexane 9/1.

Further 38.8 g of 2',3'-O-isopropylidene-5'-O-tetrahydropyranyl-8-bromo-adenosine are thus obtained (m.p. 170°-80° C. Overall yield 86%).

(ii) N,N-dimethylformamide dimethylacetal (21.4 g, 0.18 mole) is added to a suspension of the above product (24 g, 51 mmoles) in anhydrous dimethylformamide and the mixture is stirred for 18 hours. Dimethylformamide is then evaporated off under vacuum (T 40° C.) and the residue is taken up twice in toluene (100 ml×2). The resulting oil is taken up with hexane (250 ml) and triturated under stirring for 30 minutes. Upon filtration and concentration to dryness of the filtrate, the compound of the title (23.7 g) is obtained with m.p. 118°-21° C.

(R) 8-mercapto-adenosine 2',3',5'-triacetate

Acetic anhydride (11.4 ml, about 120 mmoles) is added to a solution of 8-mercaptoadenosine (6 g, 20 mmoles) in pyridine (60 ml) and the resulting mixture is stirred at room temperature for 16 hours. Methanol (30 ml) is added thereto and the mixture is evaporated to dryness. The oily residue is taken up in conc. $NH_4OH$ (5 ml)/water (100 ml) and washed with ethyl ether (100 ml). The pH is brought to 4 and the aqueous phase is extracted with ethyl acetate (2×100 ml). The combined ethyl acetate extracts are dried over $Na_2SO_4$ and concentrated to dryness to give 6.5 g of the compound of the title.

(S) 8-mercapto-2',3'-O-isopropylidene-adenosine 5'-(3,4,5-trimethoxy)benzoate

Anhydrous p-toluensulfonic acid (65.7 mmoles) is added to a stirred suspension of 8-mercaptoadenosine (5 g, 16.5 mmoles) in acetone (125 ml) and the mixture is stirred at room temperature for 2½ hours. The suspension is then poured into a solution of $K_2CO_3$ (9 g, 65.7 mmoles) in water (50 ml). The pH is adjusted to 6 by the addition of $NaH_2PO_4$, the mixture is filtered and excess acetone is evaporated off. The aqueous solution is then extracted with ethyl acetate (5×200 ml), the organic extracts are combined, dried over $Na_2SO_4$ and concentrated to a small volume. Upon cooling 8-mercapto-2',3'-O-isopropylidene-adenosine (4.5) crystallizes out. 3 g of the above product (8.84 mmoles) are suspended into a mixture of methylene chloride (30 ml) and freshly distilled pyridine (10 ml). 4-Dimethylaminopyridine (100 mg) is added to the obtained suspension and then a solution of 3,4,5-trimethoxy-benzoyl chloride (2.23 g, 9.7 mmoles) in methylene chloride (10 ml) is added thereto while keeping the temperature between 0° C. and 10° C. The reaction mixture is allowed to stand at room temperature overnight, then methanol (10 ml) is added. After 30 minutes at room temperature the reaction mixture is diluted with methylene chloride, neutralized with sodium bicarbonate, washed with water, dried over $Na_2SO_4$ and concentrated to dryness.

The residue is crystallized from toluene yielding 2.5 g of the compound of the title. As anticipated the compounds of the present invention have antihyperlipidemic activity. More particularly the compounds of the present invention show to be active in reducing plasma concentrations of VLDL (very low-density lipoproteins) and LDL (low-density lipoproteins) without affecting or even increasing, more- or less-remarkably, HDL (high-density lipoproteins).

Hyperlipoproteinemia is a sign of a heterogenous group of diseases that differ in clinical manifestation, etiology, prognosis and response to therapy. As it is known, the different types of hyperliproteinemia depend on the different types of lipoproteins that circulate in plasma as, with exception of free fatty acids, all other lipids (essentially cholesterol and tryglycerides with minor amounts of phospholipids and fatty acid esters form complexes with proteins differing in composition, size and density and, as lipoproteins, circulate in plasma. The different lipid disorders are then classified on the basis of the analysis of the hematic lipoproteins.

It has been found however that the most frequent hyperlipoproteinemias are characterized by an elevation in the concentration of low-density lipoproteins (VLDL and LDL).

Furthermore, while on the one hand there is unequivocal evidence for an association between cholesterol concentrations in plasma (which closely correlate with the concentrations of LDL in plasma LDL in plasma since 60 to 75% of the total cholesterol in plasma is normally transported in association with this lipoprotein) and the development of coronary heart disease (Circulation, 58, (1978), p. 3-19), on the other hand it has been shown a negative correlation between the plasma concentrations of HDL and the risk of coronary heart diseases (Am. J. Med., 62 (1977), p. 704-714).

It is therefore clear that an antihyperlipoproteinemic agent that, like the compounds of the present invention, lowers the concentrations of VLDL and LDL without influencing the concentration of HDL or even increasing it, represents a further step forward in the therapy of hyperlipaemia.

In particular the antihyperlipaemic activity of the compounds of the present invention has been tested in rats using male C.D. rats (Charles River) weighing, at the beginning of the experiments, about 150 g, singularly housed at an ambient temperature of 21 ±1° C., and 60% relative humidity with the room lighting operating on a 12-hour cycle.

The animals were rendered hyperlipaemic by ad libitum feeding with the modified Math diet (Sirtori C. R. et al., Atherosclerosis, 30, (1978), p. 45-46) having the following composition:
hydrogenated coconut oil—24%,
cholesterol—1%,
cholic acid—1%,
casein and vitamins—20%
mineral salts—4%,
corn oil—1%,
sucrose—49%.

Duration of the experiment was fixed in 12 days, after which the control animals showed an increase in triglycerides of about 3-4 times over the baseline value, an increase in total cholesterol of about 8-10 times over the baseline value, while cholesterol associated to HDL showed a reduction to ⅓ of the normal values.

The pharmacological treatment aimed at evaluating the oral antihyperlipaemic activity of the compounds of the invention started on day 8 ad continued until day 12 for a total of 5 administrations. Two hours after the 4th administration and with the animals fed a small blood sample was analyzed to determine triglycerides. The animals, previously fasted for 24 hours, were then sacrificed 2 hours after the 5th administration. At this time, besides abstracting the blood, the liver was abstracted in order to determine its weight as a preliminary indication of a possible hepatomegaly and for further possible analyses. To determine triglycerides, as well as for the determination of total cholesterol, a commercially available enzymatic diagnostic test has been employed. For the determination of the HDL associated cholesterol, the fractional precipitation of the lipoproteins has been accomplished by means of a magnesium chloride solution and phosphotungstic acid.

The results reported in the following table for some representative compounds of the present invention are expressed as % variation over the hyperlipaemic controls to which aqueous 0.5% carboxymethylcellulose was administered at a dosage of 5 ml/kg p.o./die. The same vehicle was employed for suspending the test compounds, which were administered at a dose of 200 mg/Kg p.o./die.

| Compound of example No. | tryglycerides | total cholesterol | HDL | Weight of the liver |
|---|---|---|---|---|
| 1 | −22 | −43 | +44 | −3 |
| 2 | −26 | −28 | +27 | +3 |
| 3 | −8 | +3 | −3 | 0 |
| 4 | +5 | −15 | +22 | −5 |
| 5 | −15 | −28 | −5 | +1 |
| 6 | −21 | −19 | +5 | −2 |
| 7 | +7 | −18 | +29 | −2 |
| 8 | −10 | −46 | +75 | −7 |
| 22 | −28 | −28 | +48 | −7 |

Furthermore the compounds of the present invention have a very low toxicity. More particularly preliminary tests carried out in mice administering an extemporaneous suspension of the compounds in aqueous 5% carboxymethylcellulose (1000 mg/Kg) showed no toxic effects. Finally, a behavioural test (Irwing test) has been carried out with the compounds of the present invention, in blind, which did not reveal any modification in the behaviour of the observed animals, at the dose of 1000 mg/kg.

For the use as antihyperlipaemics, the compounds of the present invention are preferably administered by the oral route. The new compounds may therefore be administered as capsules, tablets, coated tablets, powders, or liquid solutions or suspensions for the oral use.

Tablets and capsules may contain besides the active ingredient the conventional additives such as binders e.g. gelatin, sorbitol, polyvinylpyrrolidone and tragacanth; lubricants e.g. magnesium stearate, talc, polyethylenglycol and silica; disintegrators such as potato starch or suitable wetting agents e.g. sodium laurylsulphate; and inert fillers such as, for instance, lactose, corn starch, calcium phosphate, sorbitol or glycine.

Tablets may also be sugar-coated according to the conventional methods known in the field. Liquid preparations for the oral use may be in the form of suspensions or solutions in an aqueous or oily solvent, or in the form of emulsions, syrups, elixirs, or may be presented as powders to be mixed with the suitable aqueous or oily vehicles just before use. Such liquid preparations may contain conventional additives such as suspending agents e.g. sorbitol, methylcellulose, hydroxyethylcellulose, carboxymethylcellulose, hydrogenated edible oils such as for instance almond oil and coconut oil, propylene glycol or ethyl alcohol; and preservatives such as methyl or propyl p-hydroxybenzoate or sorbic acid.

The dosage to be administered for an antihyperlipaemic treatment depends on the particular compound employed, the weight of the subject to be treated and the particular conditions to be treated.

Typically an oral daily dosage may range between 100 and 2000 mg of active compound divided in 2–4 administrations. The compositions, either solid or liquid, which preferably contain from 50 to 99% of active ingredient, will generally contain from about 200 to about 500 mg of active ingredient per dosage unit.

We claim:

1. A compound of formula I

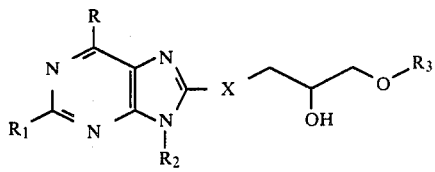

where

R is an amino, hydroxyl or keto group, $R_1$ is a hydrogen atom or an amino group, $R_2$ is a hydrogen atom or a beta-D-ribofuranosyl radical wherein the primary hydroxyl group at C-5' may be replaced by an acyloxy group, wherein the acyl may be derived from an aliphatic, aromatic or heterocyclic carboxylic acid, a carbamyloxy group or a mono-, di or tri-phosphate and the two secondary groups at C-2' and C-3' may be replaced by an acyloxy group, wherein the acyl is derived from an aliphatic carboxylic acid, or by a carbamyloxy group, $R_3$ is a substituted or unsubstituted aryl or monocyclic heteroaryl residue, and X is a sulfur or oxygen atom; either as a single pure isomer or a mixture thereof in any proportion.

2. A compound according to claim 1 wherein R is amino and $R_1$ is hydrogen or R is hydroxy and $R_1$ is amino or hydrogen, and X, $R_2$ and $R_3$ are as defined in claim 1.

3. A compound according to claim 2 wherein R is amino, $R_1$ is hydrogen, $R_2$ is as defined in claim 2, $R_3$ is a substituted or unsubstituted aryl residue, and X is a sulfur atom.

4. A compound according to claim 3 which is 8-{[[3-(4-ethoxycarbonyl)phenoxy-2-hydroxy]propyl]thio}adenosine.

5. A compound according to claim 3 which is 6-amino-8-{[[3-(4-ethoxycarbonyl)phenoxy-2-hydroxy]propyl]thio}purine.

6. A compound according to claim 3 which is 8-{[[3-(4-2-methylpropoxy)carbonyl)phenoxy-2-hydroxy]propyl]thio}adenosine.

7. A pharmaceutical composition suitable for antihyperlipidemic use, comprising an effective amount of a compound of claim 1 as active ingredient in association with a pharmaceutically acceptable carrier.

8. A composition according to claim 7 suitable for oral administration containing from 200 to 500 mg of active ingredient per unit dosage form.

9. A pharmaceutical composition useful for antihyperlipidemic use which comprises from about 200 to 500 mg of a compound according to claim 1 in association with a pharmaceutically acceptable carrier.

10. A method for reducing plasma concentration of very-low density lipoproteins and low-density lipoproteins in a patient in need thereof, said method comprising administering to said patient about 200 to 500 mg per unit dosage form of a compound of claim 1 wherein R, $R_1$, $R_2$, $R_3$ and X are as defined in claim 1.

* * * * *